United States Patent [19]
Schneider

[11] Patent Number: 5,846,080
[45] Date of Patent: *Dec. 8, 1998

[54] LASER DENTAL DEVICES AND METHODS

[75] Inventor: Richard Theodore Schneider, Alachua, Fla.

[73] Assignee: W&H Dentalwerk GmbH, Burmoos, Austria

[*] Notice: This patent issued on a continued prosecution application filed under 37 CFR 1.53(d), and is subject to the twenty year patent term provisions of 35 U.S.C. 154(a)(2).

[21] Appl. No.: 578,465

[22] Filed: Dec. 20, 1995

[51] Int. Cl.$^6$ ........................................ A61C 3/00
[52] U.S. Cl. .................. 433/215; 433/29; 606/10; 606/11; 606/13
[58] Field of Search ............ 433/29, 215; 606/9, 606/10, 11, 12, 13

[56] References Cited

U.S. PATENT DOCUMENTS

| | | |
|---|---|---|
| 3,471,215 | 10/1969 | Snitzer . |
| 3,481,340 | 12/1969 | McKnight et al. . |
| 3,769,963 | 11/1973 | Goldman et al. . |
| 3,821,510 | 6/1974 | Muncheryan . |
| 3,858,577 | 1/1975 | Bass et al. . |
| 4,045,119 | 8/1977 | Eastgate . |
| 4,120,293 | 10/1978 | Muckerheide . |
| 4,152,575 | 5/1979 | Banas . |
| 4,273,535 | 6/1981 | Yamamoto et al. . |
| 4,478,217 | 10/1984 | Shimada et al. . |
| 4,503,853 | 3/1985 | Ota et al. . |
| 4,559,942 | 12/1985 | Eisenberg . |
| 4,564,011 | 1/1986 | Goldman . |
| 4,658,817 | 4/1987 | Hardy . |
| 4,676,242 | 6/1987 | Dol . |
| 4,729,373 | 3/1988 | Peyman . |
| 4,757,515 | 7/1988 | Hughes . |
| 4,784,135 | 11/1988 | Blum et al. . |
| 4,826,431 | 5/1989 | Fujimura et al. . |
| 4,849,859 | 7/1989 | Nagasawa . |
| 4,940,411 | 7/1990 | Vassiliadis et al. . |
| 4,941,093 | 7/1990 | Marshall ........................ 606/5 |
| 5,032,445 | 7/1991 | Scantlebury et al. . |
| 5,051,823 | 9/1991 | Cooper et al. . |
| 5,055,048 | 10/1991 | Vassiliadis et al. . |
| 5,074,861 | 12/1991 | Schneider et al. . |
| 5,090,908 | 2/1992 | Teumim-Stone . |
| 5,092,773 | 3/1992 | Levy . |
| 5,116,227 | 5/1992 | Levy . |
| 5,118,293 | 6/1992 | Levy . |
| 5,122,060 | 6/1992 | Vassiliadis et al. . |
| 5,123,845 | 6/1992 | Vassiliadis et al. . |
| 5,125,922 | 6/1992 | Dwyer et al. . |
| 5,139,494 | 8/1992 | Freiberg . |
| 5,151,029 | 9/1992 | Levy . |
| 5,151,031 | 9/1992 | Levy . |
| 5,169,318 | 12/1992 | Levy . |
| 5,171,148 | 12/1992 | Wasserman et al. . |
| 5,171,150 | 12/1992 | Levy . |
| 5,173,049 | 12/1992 | Levy . |

(List continued on next page.)

FOREIGN PATENT DOCUMENTS

| 1 105 706 | 4/1984 | European Pat. Off. . |
|---|---|---|
| WO 87/02884 | 11/1986 | WIPO . |

*Primary Examiner*—Ralph A. Lewis
*Attorney, Agent, or Firm*—Merchant, Gould, Smith, Edell, Welter & Schmidt, P.A.

[57] ABSTRACT

This invention is a laser dental system for providing direct laser radiation to a desired location within a patient's mouth without the use of an optical fiber. The system directs the focal point of laser radiation to an exact location by a focus sensor and maintains focus by a positioning clamp. The focus sensor, laser pad termination system and positioning clamp also provides for control of laser radiation pulse firing. The system further includes a cooling system for cooling the surface to be engaged by laser radiation with a nonaqueous solution. The cooling system applies pulses of nonaqueous solution synchronously in between pulses of laser radiation. The system also provides for performance of surgical procedures such as root canals, whereby infected areas of a tooth are accessed through a hole drilled in the gums and jaw bone.

15 Claims, 10 Drawing Sheets

U.S. PATENT DOCUMENTS

| | | |
|---|---|---|
| 5,180,304 | 1/1993 | Vassiliadis et al. . |
| 5,188,532 | 2/1993 | Levy . |
| 5,192,279 | 3/1993 | Samuels et al. . |
| 5,194,005 | 3/1993 | Levy . |
| 5,198,926 | 3/1993 | Sheinis et al. . |
| 5,207,576 | 5/1993 | Vassiliadis et al. . |
| 5,207,673 | 5/1993 | Ebling et al. . |
| 5,228,852 | 7/1993 | Goldsmith et al. . |
| 5,232,366 | 8/1993 | Levy . |
| 5,232,367 | 8/1993 | Vassiliadis et al. . |
| 5,236,360 | 8/1993 | Levy . |
| 5,249,964 | 10/1993 | Levy . |
| 5,257,935 | 11/1993 | Vassiliadis et al. . |
| 5,267,856 | 12/1993 | Wolbarsht et al. . |
| 5,275,564 | 1/1994 | Vassiliadis et al. . |
| 5,281,141 | 1/1994 | Kowalyk . |
| 5,289,557 | 2/1994 | Sheinis et al. . |
| 5,290,273 | 3/1994 | Tan ............................................. 606/13 |
| 5,290,274 | 3/1994 | Levy et al. . |
| 5,292,253 | 3/1994 | Levy . |
| 5,299,937 | 4/1994 | Gow . |
| 5,304,167 | 4/1994 | Freiberg . |
| 5,312,395 | 5/1994 | Tan et al. ...................................... 606/9 |
| 5,318,562 | 6/1994 | Levy et al. . |
| 5,334,016 | 8/1994 | Goldsmith et al. . |
| 5,342,198 | 8/1994 | Vassiliadis et al. . |
| 5,360,426 | 11/1994 | Muller et al. ............................. 606/13 |
| 5,364,390 | 11/1994 | Taboada et al. . |
| 5,388,987 | 2/1995 | Badoz et al. . |
| 5,388,988 | 2/1995 | Goisser et al. . |
| 5,643,252 | 7/1997 | Waner et al. ................................ 606/9 |

LASER DENTAL DEVICES AND METHODS

FIELD OF THE INVENTION

The present invention relates generally to laser systems for medical use, and more specifically to laser devices and methods suited for dental applications such as treatment of abscesses, carious lesions as well as cutting or removal of soft and hard tissue.

BACKGROUND OF THE INVENTION

Laser radiation is currently employed in medicine and dentistry for performing a variety of procedures, including procedures which involve cutting or vaporizing, soft tissues, including gum, nerve tissue and pulp. It has also been demonstrated that laser radiation having a suitable wavelength and energy density can cut hard tissues, including bone, enamel, dentin and cementum, as well as demineralized hard tissues such as carious tooth tissue. Laser radiation may also be used to cut tartar, plaque or calculous, and most materials that form on tooth surfaces, as well as similar materials which accumulate in body passages, including blood vessels and urinary passages.

The effectiveness of laser radiation on any particular tissue depends greatly on the wavelength and power level of the radiation and the form in which the radiation is delivered. Typically, radiation is delivered in two ways, namely as a continuous wave or as a pulsed wave. The type of laser to be used for a particular procedure is determined by the power level and wavelength of laser light that would be most effective for that procedure. If pulsed radiation is preferable for the procedure, the optimum values for a pulse duration and repetition rate must also be determined. The energy delivered by each such pulse is the product of the laser power and the pulse duration. The energy density with which each pulse is applied to tissue being treated is the total energy delivered divided by the area of the radiation spot on the tissue. Energy density is a significant parameter in determining the effect of such laser radiation.

In procedures of the type described above, the ability to apply the radiation to a desired location is of substantial importance. In many applications, it is desirable to apply radiation by means of a handpiece which can be easily directed by the physician or dentist. Since, however, lasers themselves, particularly those which produce the power levels required by such medical treatments, are relatively bulky devices, hand pieces are used in conjunction with optical fibers for conducting the laser radiation from the laser itself through the handpiece. One of the problems associated with the use of optical fibers for transmitting laser radiation is that for certain laser wavelengths the material to be used for the fiber cable may be brittle, and therefore subject to breakage. In addition, the coherence characteristics of laser radiation is deteriorated after traveling through a fiber.

Although radiation produced by many lasers currently in use cannot be satisfactorily transmitted via optical fibers, it is known that radiation wavelengths from about 0.5 micrometers up to about 1 micrometer can be transmitted via conventional optical fibers. At longer wavelengths there are absorption bands, especially around 3 micrometers.

On the other hand, hand-held lasers that are small enough for use in dental applications that do not use optical fibers have other problems. Without an optical fiber, the surgeon must direct the focal point of the laser radiation at the item to be engaged. It would be very difficult for a dental surgeon to maintain precise positioning distance along with keeping a steady hand. Both would be necessary to properly direct the laser radiation focal point for an optimal surgery. The difficulty may be further compounded because energy existing from a laser dental device is typically infrared. It would be very difficult for a surgeon to direct the laser radiation focal point to its correct location if it is not visible. The problem with infrared laser radiation has been solved in the past by designing the dental device such that visible light can be directed along the same axis having the same focal point as the laser radiation. The visible light allows the dentist to properly align the dental instrument so that the laser radiation focal point is directed at the appropriate target. However, visible light does not solve the problem associated with an unsteady hand. There is a need for a dental system that does not use optical fibers that can maintain a constant position and distance from the surface to be engaged by laser radiation.

Laser radiation having a wavelength of less than 3 micrometers includes those produced by the Nd:YAG laser (fundamental wavelength 1.06 micrometers) and the Er:YAG laser (fundamental wavelength of 2.94 micrometers). Both of these forms of laser radiation are capable of cutting various types of tissue, although each employs a somewhat different mechanism to do so. This difference results in part from the fact that water has a very low coefficient of absorption for laser radiation at the wavelength of 1.06 micrometers and a relatively high absorption coefficient for radiation at the wavelength of 2.94 micrometers. It is known in the art that appropriate lasers for use in dental applications are Er:YAG and to a lesser degree Nd:YAG. The reason being that the Er:YAG radiation coincides with a major absorption band of water.

Erbium (Er) is a chemical element of the rare-earth group that occurs with yttrium and is also used as a source of laser irradiation. An Er:YAG laser is a solid state, pulsed laser which has a maximum emission in the mid-infrared region at 2.94 micrometers and water absorbs strongly in this region. Laser surgery performed with an Er:YAG laser results in the water in the target tissue absorbing radiant energy.

A hard surface, such as a tooth, although it has very little water, is nevertheless heated by absorption of laser radiation. When laser radiation is applied to a tooth, in order to prevent damage to the pulpal, which is living tissue, the tooth needs to be cooled simultaneously with the laser radiation treatment. In the past, water spray, air spray or a combination of both have been used to cool hard surfaces such as teeth.

Water spray has been used in conventional dental surgery and in laser dental surgery as a coolant for the surface treated after a pulse of radiation. For example, the patent of Vassiliadis et al. (U.S. Pat. No. 4,940,411) discloses a dental laser using a Nd:YAG laser. In this patent, water is sprayed on the tooth after a pulse, followed by drying of the tooth prior to subsequent activation of the pulse laser.

Other methods of cooling are implemented through the use of controlled addition of water, rather than drying of the surface, prior to and/or during laser surgery, so that no more than a thin film of water is present during surgery. The effect of spraying water to achieve a thin film is intended to cause a significant increase in laser efficiency and less residual damage than with prior laser surgery methods for hard materials. However, spraying of water is counter-productive for hard surfaces being treated because the water absorbs Er:YAG laser radiation significantly when the water on the surface accumulates to more than a few micrometers thick. On hard materials, such as teeth, having a non-uniform surface comprised of significant indentations, water accumulates in pockets that are greater than a few micrometers. The effect of such accumulation minimizes the effectiveness of laser interaction with the surface area covered by the pocket of water because the water absorbs the laser radiation.

Cooling hard surfaces with air is also counterproductive because air encourages the formulation of thermal gradients in the tooth that can cause cracks in the tooth. There is a need for a method of cooling hard surfaces such as teeth that can provide uniform cooling to non-uniform surfaces without causing the damage described above.

Dental devices are known to be used in performing surgical procedures, such as a root canal, to gain access to infected areas of a tooth. A root canal is a surgical procedure used when a tooth becomes afflicted with a lesion or abscess. The infected area is most likely to appear near the root of the tooth, and can be inside the tooth root or outside of it. It is a known procedure to drill a canal from the top of the tooth into the root to access the infected area. The contents of the root (nerve and blood vessels) are removed (meaning the tooth is killed) and medical treatment is performed through this canal. After medical treatment, the canal is filled with a suitable material.

It is also possible to perform a root canal surgical procedure by way of removing a part of the gum tissue as well as a part of the jaw bone to gain access to the root of the infected tooth. Abscesses are then removed. The bone tissue is then covered with gum tissue and the healing process would require some time as a result of the size of the hole in the jaw bone. It is difficult to drill small holes when the tissue being engaged by the drill bits are on both extremes, soft and hard. There is a need for a system that provides for access to the infected area of a tooth through small holes that are created. Small holes would drastically reduce the healing time associated with this procedure.

SUMMARY OF THE INVENTION

The present invention is a laser dental system including a laser dental device comprised of a laser source within a housing, an emission head attached to the housing for receiving and transmitting laser radiation from the laser source, a focus sensor attached to the emission head for positioning the emission head at an optimal distance from the surface to be engaged by laser radiation. The laser dental device may also include a locking system attached to the emission head for removably locking the dental device in position during surgery.

The present invention also comprises a beam rotator with the above-described laser dental device, wherein the emission head of the laser dental device includes the beam rotator which is comprised of a central mirror and a slidably adjustable outer mirror within a rotating housing. The beam rotator is positioned at a first end of the emission head for rotating laser radiation received from the laser source. The slidably adjustable outer mirror is used to increase or decrease the circumference of the hole to be drilled by rotating laser radiation transmitted from the emission head.

The laser dental system of the present invention is a combination of the laser dental device described above with a cooling system. The cooling system is electromechanically controlled by the laser source of the laser dental device and provides a means for cooling the surface to be engaged by laser radiation. The cooling system sprays a nonaqueous solution onto the surface to be cooled between each pulse of laser radiation.

The focus sensor of the present invention provides for the positioning of the dental device in proximate location with the surface to be engaged by laser radiation so that the laser radiation focal point is located at the desired position on the surface to be engaged. The laser dental device locking system provides for temporary locking of the laser dental device in position so that the laser light focal point will remain stationary at the selected area of the surface to be engaged.

The present invention also provides for performance of a surgical procedure on an infected area of a tooth using laser radiation emitted from a laser dental device. The laser dental device is positioned such that its emission head is in association with the infected tooth such that the focal point of the laser radiation is directed at the infected area of the tooth. The laser radiation being directed through the patient's gum and jaw bone for creating an opening in the gums and jaw bone to allow for laser radiation engagement with the infected area of the tooth. During laser radiation engagement, the head of the laser dental device is stabilized so that the focal point of the laser radiation remains directed at the infected area of the tooth through the gums and jaw bone. Having so obtained access to the infected area of the tooth, the infected area is drained and treated with medication.

GENERAL DESCRIPTION

In accordance with the teachings of this invention, a dental system includes a laser dental device which allows the dental practitioner to direct laser radiation to a desired location within a patient's mouth without the use of an optical fiber. The dental system also includes a cooling system for cooling the surface to be engaged by laser radiation emitted from the laser source. Laser radiation is directed to an exact location by the dental device's focusing sensor and system focusing is maintained by the dental device's locking system. Focusing laser radiation so that the focal point of the laser beam is directed at the correct location and maintaining that location with a locking system allows the dental practitioner to perform surgical procedures with accuracy and minimal errors. The dental system's cooling system functions simultaneously with laser radiation interaction, allowing the practitioner to perform surgical procedures in shorter periods of time. Simultaneous cooling reduces the need to disengage laser treatment to allow for cooling of hard surfaces such as teeth.

In order to minimize the effect of small unavoidable vibrations, the emission head of the laser dental device must be positioned in close proximity to the surface to be engaged with laser radiation. The closeness of the emission head to the surface to be treated requires that the laser dental device or laser source is compact. A compact laser source is one that is small enough to fit into a laser dental device handpiece or a laser source within a laser dental device that is configured such that the emission head of the laser dental device can be can be suspended by a stand next to the face of the patient to be treated, similar to an X-ray tube.

DETAILED DESCRIPTION OF THE DRAWINGS

Figure 1:
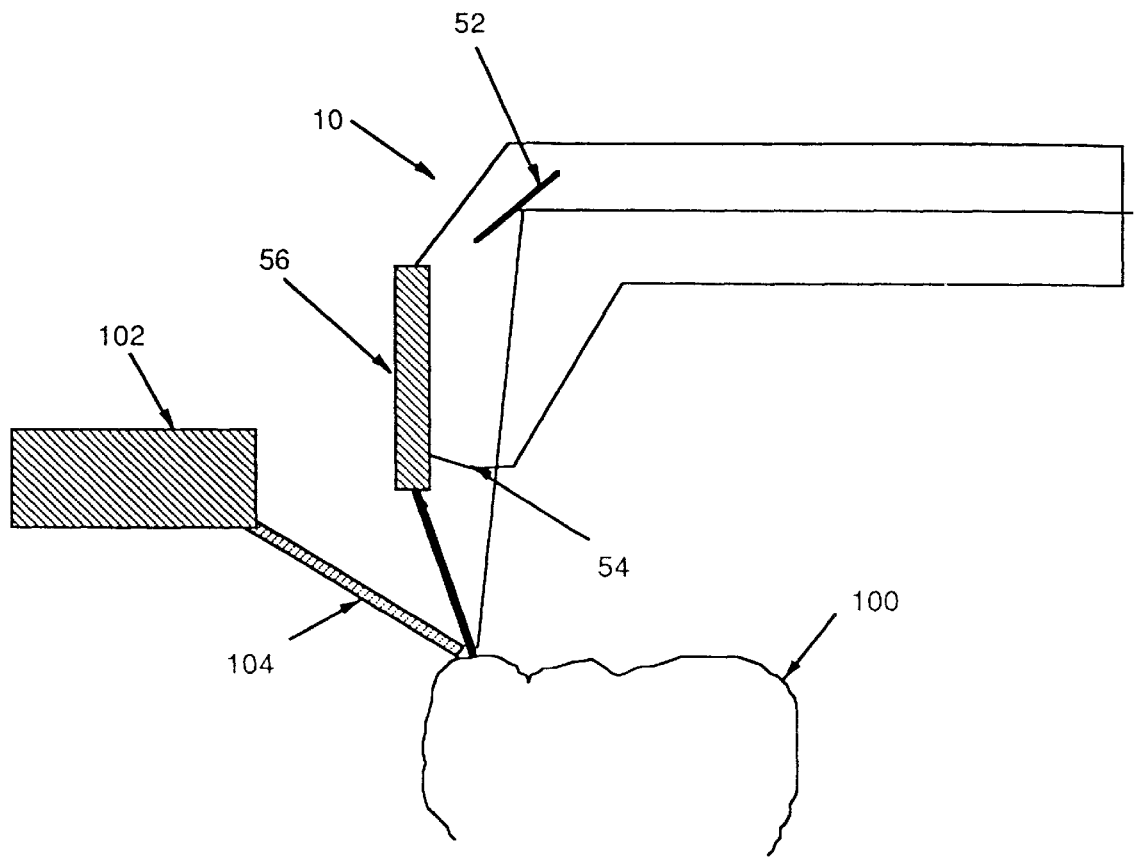
FIG. 1 is a schematic view of a laser dental device which can engage a surface with laser radiation and simultaneously cool the surface to be engaged.
Figure 2:
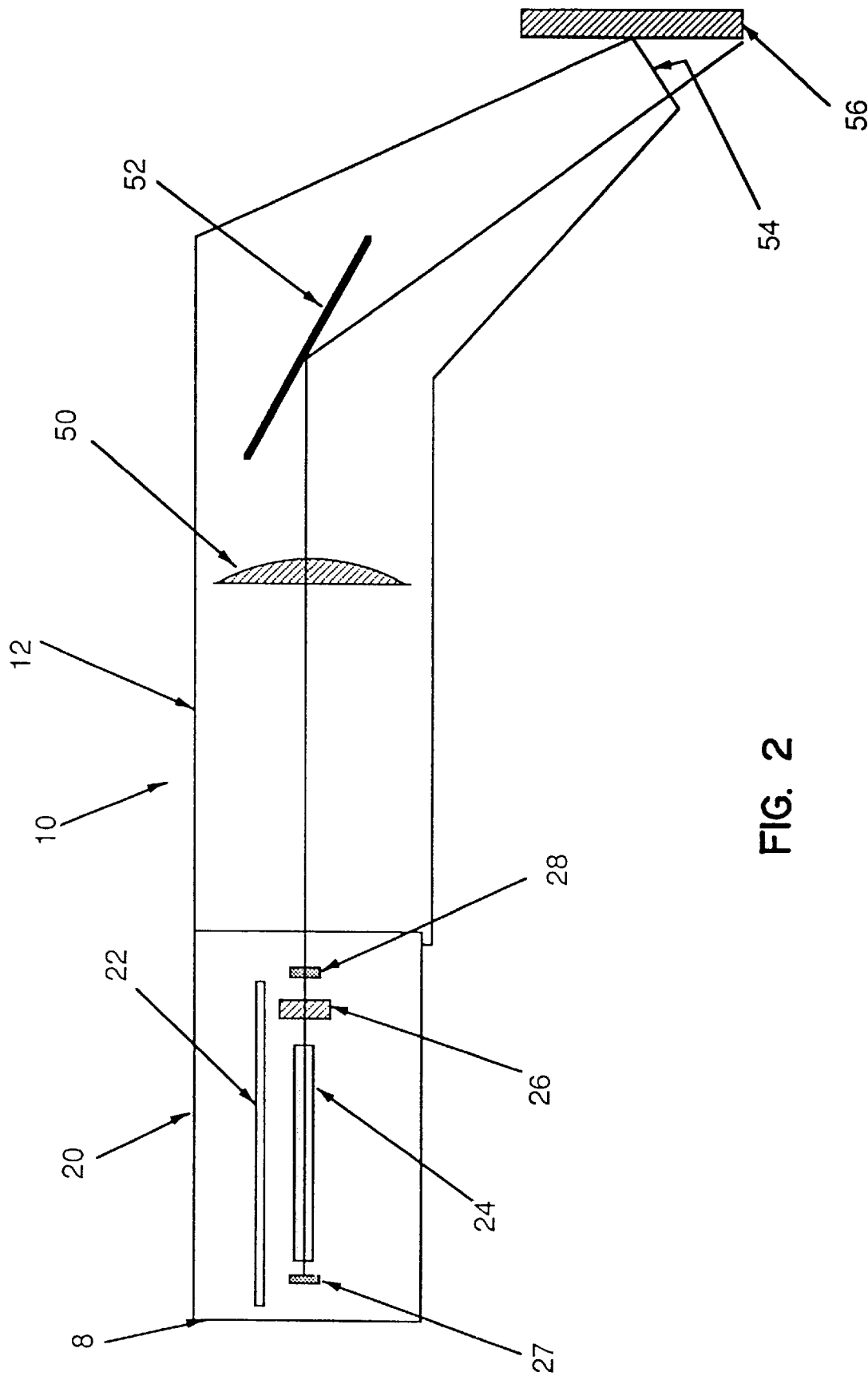
FIG. 2 is a longitudinal sectional view illustrating the basic components of a device constructed to perform various dental treatments according to the invention.

FIGS. 1 and 2 show a view of one embodiment of a laser dental device 10, of the laser dental system, constructed in accordance with the teachings of this invention. The laser dental device 10 includes a hand piece 12 suitable for being held in the hand by an operator and a laser source within a housing 20. At the proximal end 8 of the dental device 10 is located one or more connectors (not shown) for connection of the dental device 10, via an electrical cable assembly (not shown) to a cooling system (not shown). In other embodiments, the connectors are in the power supply.

The laser source is comprised of a flashlamp 22, laser rod 24, Q-switch 26 and laser mirrors 27 and 28. One or more flashlamp 22 acts as a pump for the laser light source. Flashlamp 22 is located longitudinally parallel to the center axis of emission head 12 and produces very brief, intense flashes of light, approximately 1 to 100 pulses per second.

The laser rod 24 is positioned longitudinally along the center axis of emission head 12 and parallel to housing 20. The laser source within housing 20 includes at least 2 mirrors 27 and 28. The first mirror 27 of the laser is totally reflective and the second mirror 28 of laser source 22 is partially reflective. Optionally, a Q switch may be added. The Q switch is used to generate large output bursts of radiation from the laser source. The bursts of radiation are accomplished by effectively blocking the optical path to the second mirror 28 for a length of time during which the rod is being pumped, causing the rod to store energy. The Q switch then quickly restores the optical path to the mirror and a giant pulse is generated.

The laser rod 24 may be comprised of either one of the following materials: Er:YAG, Nd:YAG, Ho:YAG, CTE:YAG, ErCr:YSGG. However, in the embodiments disclosed in FIGS. 2 and 2A, the laser rods are Er:YAG. Using an Er:YAG laser, it is preferred for removal of material, that laser radiation needs to be pulsed. Each pulse of laser radiation has energy in the range of 50 milli-joules to 500 milli-joules. The number of pulses needed is between 5 hertz and 50 hertz. The pulse width needs to be between 0.1 micro seconds and 300 micro seconds. Alternatively, if an Nd:YAG laser is used, the laser energy per pulse needs to be 10 milli-joules and 400 milli-joules. The pulse width needs to be between 10 and 50 nano seconds for Q switched operation and between 1 micro second and 300 micro seconds for operation without the optional Q switch.

An Er:YAG laser rod is used in the laser dental device disclosed in FIG. 2 particularly because it generates light at about 2.94 micrometers. As such, Er:YAG radiation coincides with a major absorption band of water. Er:YAG laser radiation is of low energy. It is also of a wavelength readily absorbed by materials found in the body, such as hydrocarbons and water. When laser radiation engages hard surfaces, such as teeth, the surface engaged will need to be cooled.

Figure 2A:
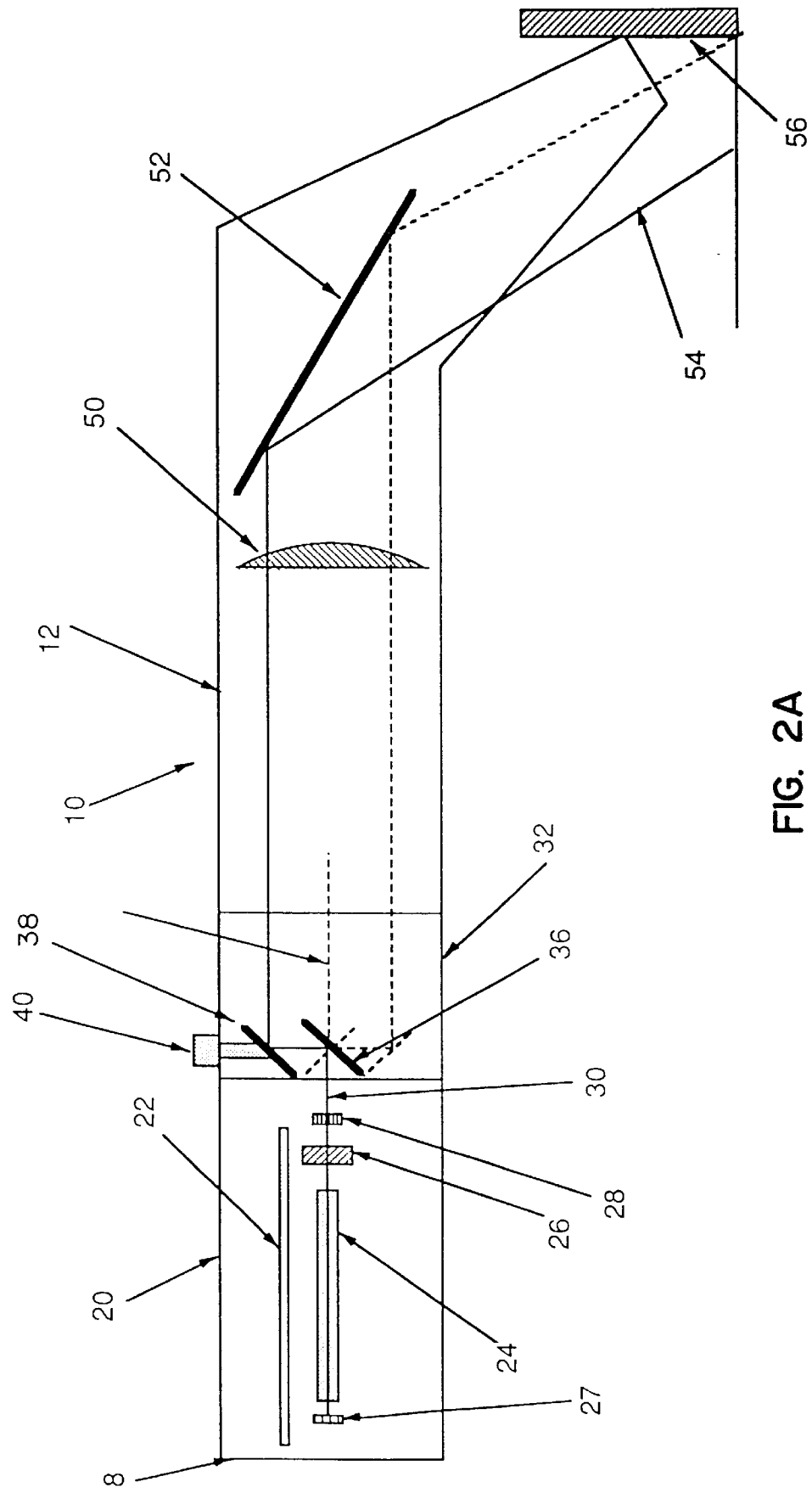
FIG. 2A is a view similar to that of FIG. 2 of an embodiment including the system beam rotator of the present invention.
Figure 2B:
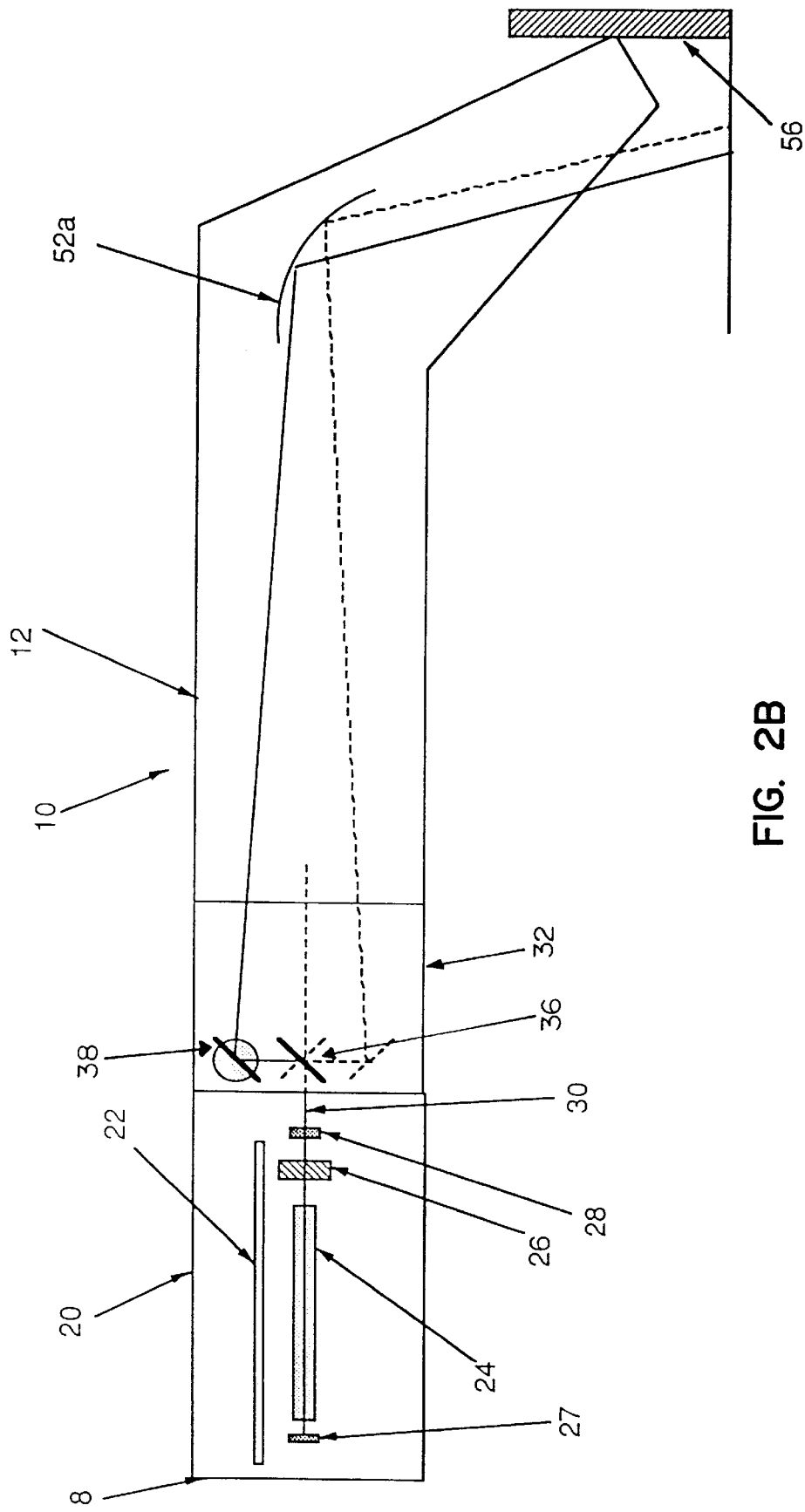
FIG. 2B is a view similar to that of FIG. 2A of an alternate embodiment of the present invention including the system beam rotator.

The laser radiation generated in laser source 20, upon exiting through second mirror 28, as shown in FIGS. 2A and 2B, enters and exits the beam rotator 32 and enters the emission head 12. Upon entry of emission head 12, laser radiation travels longitudinally and is focussed by a non-flexible light guide, focusing lens 50. In other embodiments, a light horn or cylindrical rod may be used as a non-flexible light guide in place of focusing lens 50.

After the laser radiation has been focussed, it engages redirection mirror 52. Redirection mirror 52 is pivotally mounted within the emission head. Redirection mirror 52 serves to redirect laser radiation to any desired angle from its longitudinal direction. An angle between the optical axis of emission head 12 and the mirror 52 normal is within the range of approximately 30 to 60 degrees is often useful. Redirection of the laser radiation allows the surgeon to access all locations on the surface to be treated.

In FIGS. 2A and 2B, an alternative embodiment of the dental device 10 is shown. The embodiment in FIG. 2B utilizes a concave mirror 52a as the focusing means instead of focusing lens 50 and redirection mirror 52 as shown in FIGS. 2 and 2A. Concave mirror 52a performs both functions of focusing and redirecting laser radiation to a desired angle.

Figure 3:
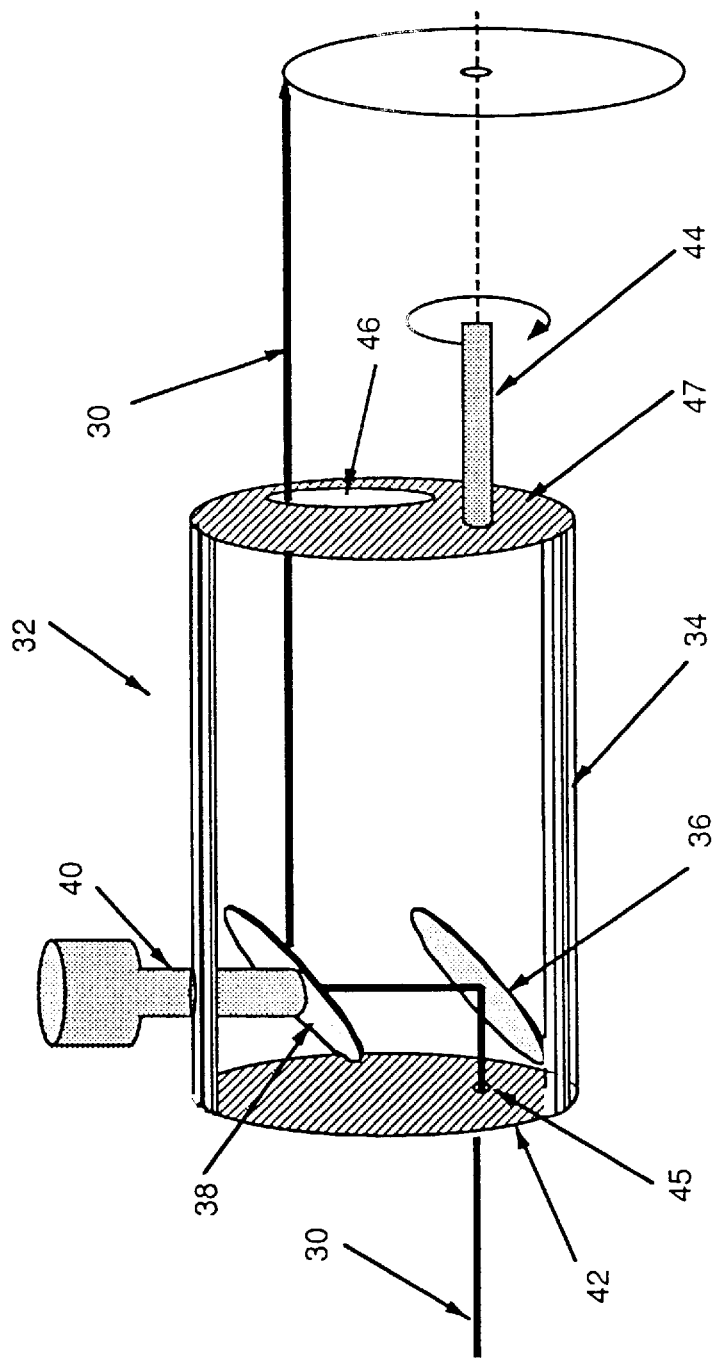
FIG. 3 is a longitudinal sectional view illustrating the basic components of the present invention's beam rotator.

The beam rotator 32 is positioned between the laser source 20 and emission head 12 as shown in FIGS. 2A and 2B. As shown in FIG. 3, the beam rotator is comprised of an adjuster 40, first and second mirrors 36 and 38 and a housing 34. The beam rotator 32 is positioned along the longitudinal axis of the emission head 12 and along the direction of travel of laser radiation. At a first end 42 of the beam rotator 32, an orifice 45 allows entry of laser radiation 30 from the laser source. Orifice 45 is positioned at the axis of rotation 44 of the beam rotator 32 which is along the axis of laser radiation 30. Laser radiation entering the beam rotator 32 through orifice 45 is reflected 90 degrees by first mirror 36 and is redirected into second mirror 38 where it is also reflected 90 degrees so that the laser radiation direction of travel is parallel to the laser beam axis, but shifted off-axis by a desired amount. Beam rotator 32 has a second orifice 46 at its second end 47 to allow for exiting of laser radiation. Beam rotator 32 also includes a motor (not shown) and appropriate gearing (not shown) attached to the beam rotator 32 causing the beam rotator 32 to rotate about its axis of rotation.

When beam rotator 32 is rotated about its axis, the laser radiation 30 existing from beam rotator 32 and traveling through emission head 12 describes a circle or spiral at the output of hand piece 12. The circle or spiral drills a cylindrical cavity into the surface engaged by the rotating laser radiation. With the aid of adjuster 40, the circumference of the circle or spiral described by rotation of beam rotator 32 can be increased or decreased by rotation of second mirror 38 or increasing or decreasing the distance between first and second mirrors 36 and 38. Adjuster 40 is a cylindrical rod having a head at its first end. Attached at the second end of adjuster 40 is second mirror 38. The normal of second mirror 38 forms a 45 degree angle with the axis of adjustor 40. Adjuster 40 extends through an orifice within the emission head 12 and slidably or threadingly engages the emission head 12 walls to allow for increase and decrease of the distance between first and second mirrors 36 and 38.

With proper focusing, it is possible to drill holes as small as 200 micrometers in diameter that can have any desired depth. The ability to drill holes of this size can be used, for example, to access through the gum, abscesses outside or inside a tooth. The hole would be used to drain the abscess or inject medication to the infected site.

Figure 4:
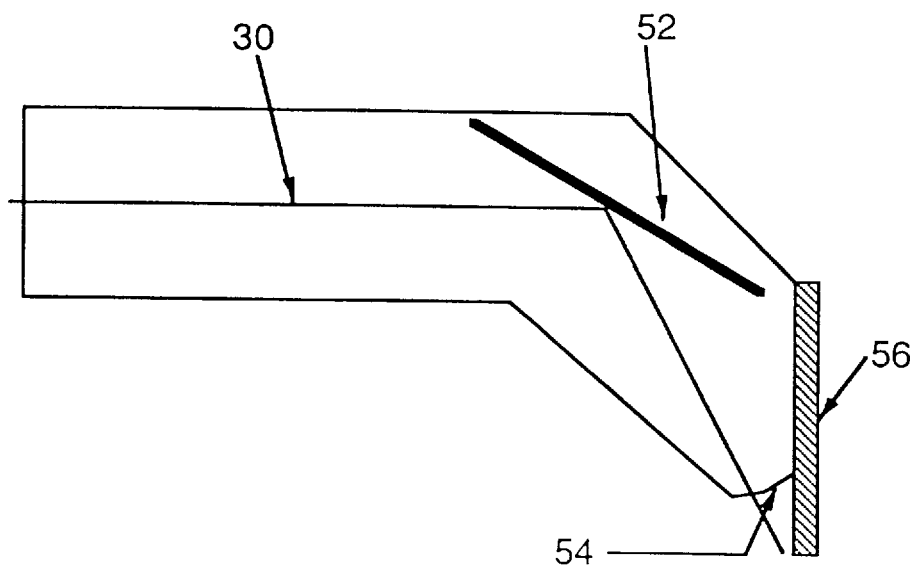
FIG. 4 is a block diagrammatic longitudinal sectional view of the front end of the present invention indicating reflections at a bend in the device.

FIG. 4 illustrates the front end of emission head 12 of laser dental device 10. The front end of emission head 12 is where mirror 52 is located. Mirror 52 redirects laser radiation traveling through emission head 12 and out of emission head face 54. The direction of laser radiation exiting emission head face 54 can be controlled by movement of mirror 52.

In order to maintain proper focusing during operation of the dental device, emission head 12 has to maintain a constant distance from the tooth within tolerance on the order of less than a millimeter. Since laser radiation is focussed into a spot, it is important to guarantee that this spot is maintained on the surface requiring laser interaction. The radiation generated by laser rod 24 utilized in the present invention is infrared in most cases and therefore not visible. Therefore focusing of laser radiation by observation is not possible. Focusing may be performed using a visible laser beam superimposed to the infra red laser beam. While this is a common practice, it is not very suitable for the present application. Dust and vapor rises from the laser radiation impact point and obscures any visible observation. Therefore, alternatively the present invention teaches using mechanical sensing means.

Figure 5:
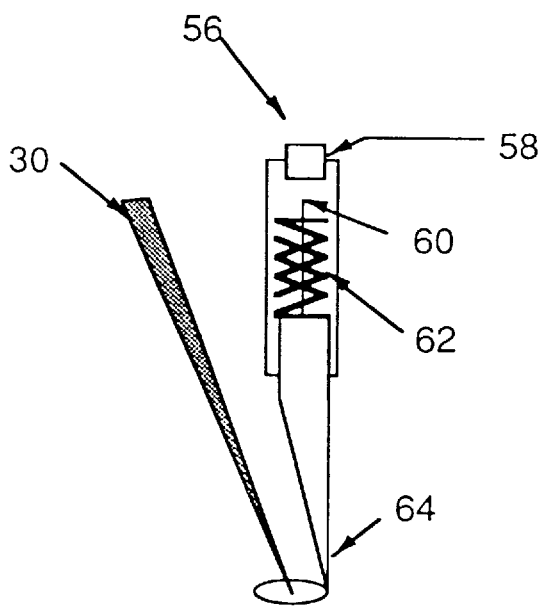
FIG. 5 is a side elevational view illustrating the basic components of the present invention's focus sensor.

The focus sensor 56 shown in FIGS. 4 and 5 provides the laser dental device with the ability to perform as a stand off device, wherein the laser is positioned such that the part of the radiation field that is most efficient for removal of tooth material, is placed on the surface or into a cavity of the tooth. This is accomplished by pressing the hand piece down onto the surface to be treated until contact 58 is activated. The focus sensor also provides the laser dental device with a means for controlling emission of laser radiation until focusing is attained.

As shown in FIG. 5, the focus sensor includes a feeler 64 attached to a spring 62 and pin 60, a housing 66 and contact 58 positioned at the closed end of housing 66. The spring 62 is attached at one end to the side walls of the housing. Therefore, when the hand piece 12 is pressed down upon the surface to be engaged, spring 62 is compressed and pin 60 moves upward to engage contact 58. Upon engagement of pin 60 with contact 58 the dental practitioner is notified by way of an electrical signal that proper focusing has been achieved. This signal can be used to provide audible or visible indication as well as control to an interlock that prevents the laser from being fired when focusing is not achieved. It should be noted that acceptable focusing can be achieved over a certain range in the laser beam waist. This range depends on the focal length of the focusing lens used, and on the original beam diameter. Therefore, the contact 58 shown in FIG. 5 may be a sliding contact 58 that will be closed over the total range of acceptable focus.

Figure 6:
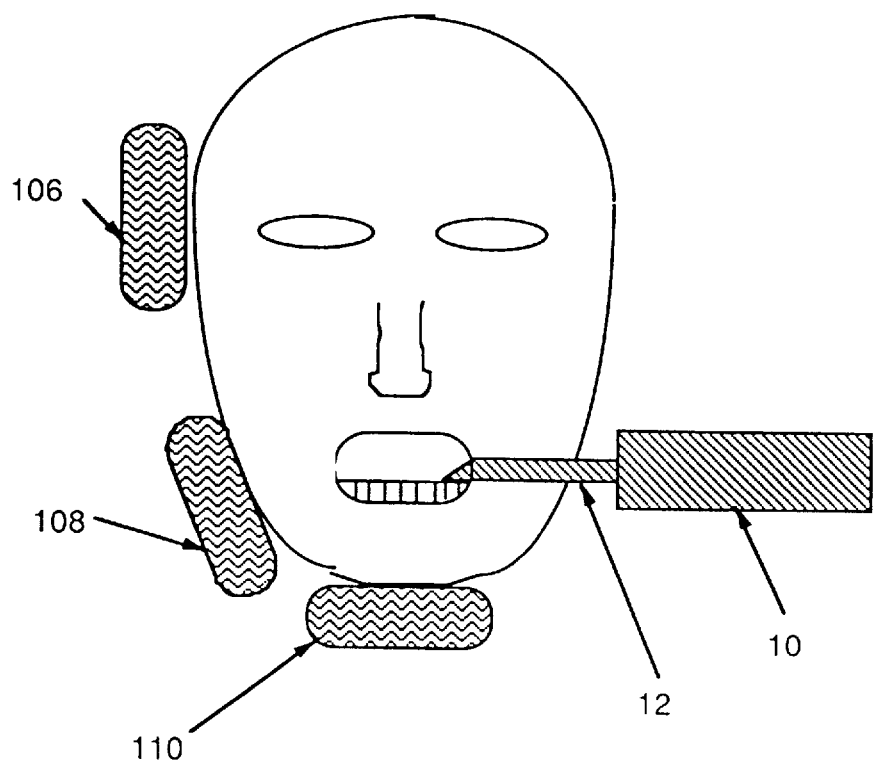
FIG. 6 is a perspective view of a head rest pads of the laser termination system of the present invention.

An important feature of the mechanism is to provide for safety, namely that the laser will not fire unless it is on target and properly focussed. Such a mechanism is shown in FIG. 6. A patient is provided with three reference pads, 106, 108 and 110 and is encouraged to press his/her face against the three pads. The patient is not physically restrained and the head engages reference pads, 106, 108 and 110 by the patients own free will. The reference pads include sensors that are electrically connected to the laser dental device 10. If the patient decides to move, laser radiation is automatically terminated. The sensors within the reference pads may be sensitive to a plurality of different external forces such as pressure, movement, or heat. It is to be understood that the reference pad sensitivity is not: limited to the above forces. Reference pad sensitivity is meant to include any external changes with respect to patient movement with respect to the reference pads.

Figure 7:
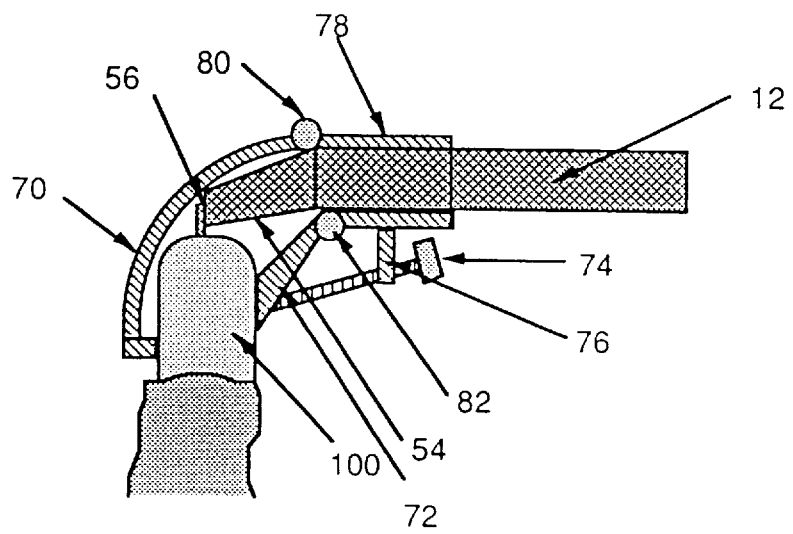
FIG. 7 is a longitudinal sectional view of the present invention's locking device engaged on a tooth.

The laser dental device also includes a locking mechanism attached to the head of the hand piece as shown in FIG. 7. The locking mechanism assists in keeping the laser radiation in proper focus. The locking mechanism includes first and second clamping arms 70 and 72 that are attached to a base 78 by spring loaded joints 80 and 82 that are attached to the emission head 12 through base 78. The spring loaded joints 80 and 82 of clamping arms 70 and 72 release the grip upon tooth 100 if patient movement becomes excessive. The second clamping arm 72 also includes a lock 74, 76 that is threadingly engaged to lock arm 72 tightly to the tooth 100. Each clamping arm 70 and 72 also includes positioning heads (not shown) attached at the end of each arm for engaging the surface clamping arms 70 and 72 are attached thereto.

Prior to application of clamping arms 70 and 72 to the tooth 100 being treated, an optional procedure is to have the tooth 100 and its two neighboring teeth covered with a fast setting plastic material. When applying this material, care must be taken so that a smooth surface is obtained. The positioning heads of each clamping arm 70 and 72 has a locator pin (not shown) that will dig into the plastic material. Therefore, if clamping arms 70 and 72 are removed for any reason, they can be reset into their original location by inserting the locator pins of the positioning heads into the holes within the fast setting plastic material that were originally dug by the locator pins.

Figure 8:
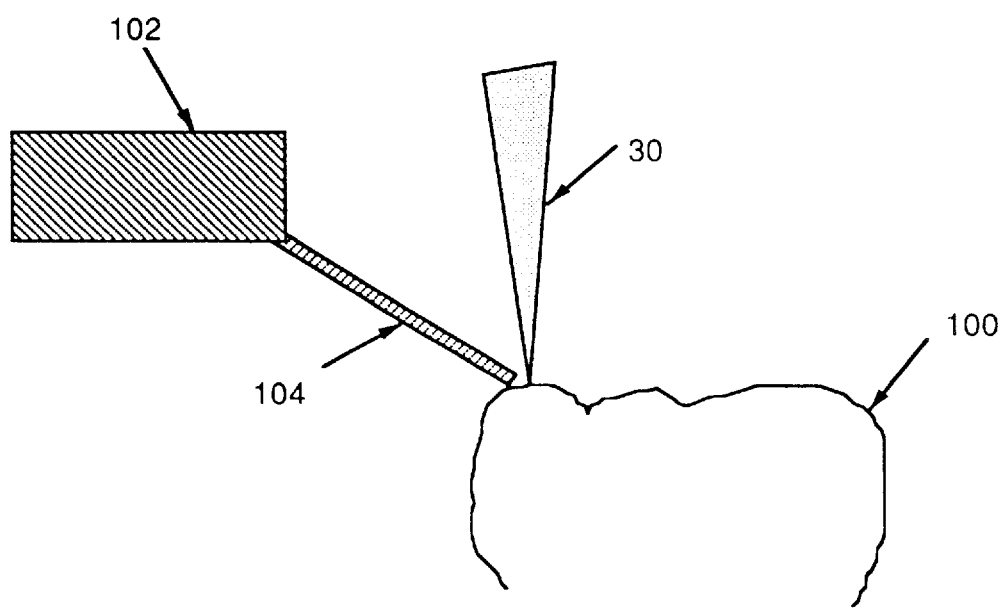
FIG. 8 is a perspective view of a laser dental system comprised a laser dental device and cooling system engaged on a tooth embodying principles of the present invention.

FIG. 8 illustrates the coolant applicator portion of the system used in conjunction with the laser dental device. The coolant applicator is electrically interconnected with the laser dental device 10 to allow for application of a predetermined amount of a nonaqueous fluid over a selected area of the surface interacted with pulses of laser radiation. The nonaqueous fluid that may be utilized in conjunction with Er:YAG laser radiation should be transparent, not contain water and must have a low vaporization point. Solutions that may be used include ethyl alcohol, benzyl acetate, furfuryl acetate or any other organic solvent that is not harmful to the patient. The low vaporization point of the nonaqueous fluid is very important because the latent heat (heat of vaporization) can be used to cool the tooth. The latent heat also allows the tooth to dry itself as a result of fluid evaporation.

The coolant applicator includes a pulsator 102 which controls distribution of the nonaqueous solution. The pulsator is electrically interconnected with the laser dental device 10 such that the pulsation of nonaqueous solution occurs between pulses of laser radiation. The nonaqueous solution is applied by a capillary tube 104 with an orifice that is positioned close to the laser radiation impact site as depicted in FIG. 8. In case of pulsed operation of the laser a very well metered amount of nonaqueous solution is sprayed on this site between each pulse. The area covered by the nonaqueous solution should be similar in size to the footprint of laser radiation. The laser radiation will penetrate the nonaqueous solution with minimal absorption. However, whatever heat is generated on the tooth surface resulting from laser radiation interaction will be taken up by the nonaqueous solution as heat of vaporization before it can migrate into the tooth.

Figure 9:
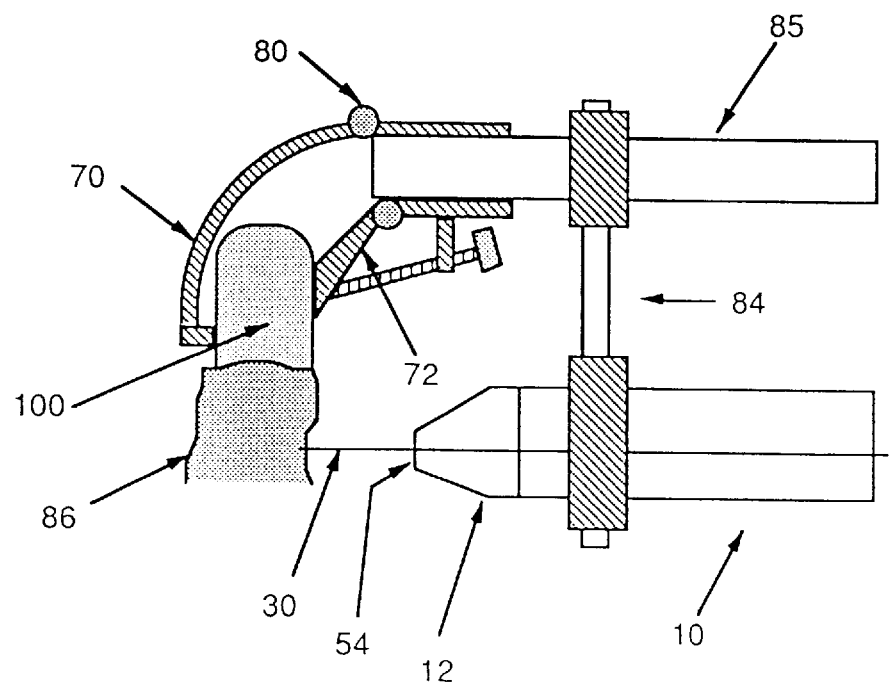
FIG. 9 is a longitudinal sectional view of the present invention's locking device engaging a tooth and positioning a laser dental device such that its head provides for engaging a laser radiation of a tooth from the side, through the gum and jaw bone.

In FIG. 9, the laser dental system of the present invention illustrates use of the locking mechanism along with a gum line surgical attachment 84 connected between the laser dental device 10 and emission head 12. Both laser dental device 10 and, emission head 12 are attached to the locking mechanism through the gum line surgical attachment 84.

In FIG. 9 a simple cylinder 85 replaces the emission head 12 that is shown in FIG. 7. In FIG. 9 the gum line surgical attachment 84 holds the laser dental device 10 and emission head 12 at a level that make penetration of the gum possible.

The gum line surgical attachment 84 may be used in conjunction with the laser dental device 10 in performing a new and improved microsurgery procedure that involves accessing the root of an infected tooth. The infected area may be accessed by the normal procedure of drilling a canal from the top of the tooth down into the infected area. The infected area may be accessed by drilling a hole from the side through the gum and jaw bone.

The infected area of the tooth is engaged with laser radiation emitted from the emission head 12 of the laser dental device 10. The procedure consists of positioning the emission head face 54 of laser dental device 10 in association with the infected area of the tooth such that the focal point of the laser radiation emitted from the laser dental device is directed at the infected area of the tooth. The laser dental device is then stabilized so that the dental device emission head face 54 maintains focus of the laser radiation focal point directed to the infected area of the tooth. Because of the positioning of the infected area (near or inside the root of the tooth), the laser radiation is directed through the patient's gums and jaw-bone and drills a small canal therethrough before engaging the infected area of the tooth. After the infected area of the tooth has been accessed, the abscess or lesion is drained by way of suction through the small canal. The infected area is then treated by injection of antibiotics into the small canal.

The optimal size of the small hole drilled through the gum and jaw bone through laser interaction ranges between 0.2 millimeters and 1 millimeter. Although it is possible to drill larger holes, the present procedure typically maintains the small hole in the range of 0.2 to 1 millimeter. Holes that are larger than 1 millimeter tend to require longer periods of time for healing.

The use of laser radiation for purposes of drilling a hole through the gum and jaw bone is preferred over the use of a mechanical drill that utilizes bits because of the varying tissues that a surgeon must drill through before accessing an infected area in the root of the tooth. The surgeon must drill through soft tissue as well as bone. A mechanical drill that utilizes bits requires two separate drill bits for the varying tissues and would have difficulty achieving a hole size small enough, such a 0.2 mm.

As shown in FIG. 9, the laser dental device 10 is clamped 70, 72 to the jaw and positioned in a way that the laser beam 30 can penetrate the gum 86 and jaw bone (not shown) to hit the abscess within the root of the tooth with the laser beam focal point. The positioning of the laser dental device 10 will be determined by the location of the infected area within the tooth. The position of the infected area would be determined beforehand through x-rays. Once the small canal is created in the gum, jaw bone and tooth, the laser dental device would be moved and the contents of the abscess drained by application of a slight vacuum through the canal which has been drilled. Medication would be injected into the hole by slight overpressure.

Figure 10:
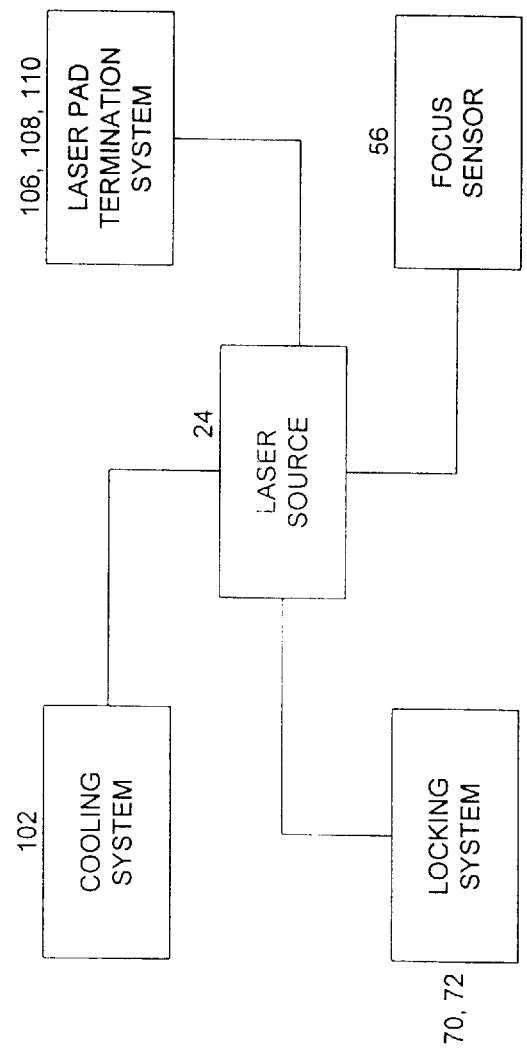
FIG. 10 is a block diagram of the laser dental device system illustrating electrical connections of the individual components.

As shown in FIG. 10, the laser dental device system has a plurality of elements all electrically connected. The laser source 24 is electrically interconnected to the focus sensor 56, the locking system 70, 72, the cooling system 102, the laser pad termination system 106, 108, 110 and in some embodiments the beam rotator 32. Focus sensor 56 is electrically interconnected to laser source 24 to provide the additional function of a means for controlling the emission of laser radiation, only allowing laser radiation firing when the emission head of the laser dental device is in proper focusing distance. The locking system 70, 72, is electrically connected to the laser source also performing as a controller of emission of laser radiation. The locking system 70, 72 also acts as an emission head stabilizer and terminates laser radiation emission when the laser head is subjected to significant movement. The laser pad termination system 106, 108, and 110 also performs as a laser radiation control mechanism by way of terminating laser radiation emission when a patient becomes restless and head movement is significant.

The cooling system 102 is electrically interconnected to the laser source because the laser source and cooling system must be synchronized to allow for application of a predetermined amount of nonaqueous solution between each pulse of laser radiation.

It is to be understood that while certain embodiments of the present invention have been illustrated and described, the invention is not to be limited to specific forms or arrangement of parts herein described and shown. Changes can be made in detail especially in matters of shape, size and arrangement of parts within the principles of the present invention to the full extent indicated by the broad general meaning of the appended claims.

What is claimed:

1. A laser dental device comprising:

a housing;

a laser source including a flashlamp within said housing for generating a laser beam when said laser source is fired;

an emission head having a first end and a second end wherein said first end is attached to said housing, said laser beam passing through said emission head to said second end; and a focus sensor attached to said second end of said emission head for positioning said emission head at a predetermined distance from a surface of a patient's mouth to be engaged by said laser beam, said focus sensor including a movable feeler member having an actuator that enables said laser source so that said laser source continuously fires when said emission head is within a range of distances that allow said laser source to engage the surface of a patient's mouth across the entire beam waist of said laser source.

2. The laser dental device of claim 1, wherein said focus sensor continuously emits an electrical signal that causes said laser source to fire when said emission head is positioned within said range of distances from the surface of a patient's mouth to be engaged by said laser source, said electrical signal resulting from a switch being closed when said actuator is in predetermined positions.

3. The laser dental device of claim 1, further comprising a locking system attached to said second end of said emission head for removably locking said emission head to the patient.

4. The laser dental device of claim 3, wherein said laser locking system is electrically coupled to said laser source for automatically terminating said laser source when said locking system is disengaged.

5. The laser dental device of claim 1, further comprising a cooling system electrically coupled with said laser source for cooling the surface of the patient's mouth by applying pulses of predetermined amounts of a nonaqueous solution to the surface of the patient's mouth.

6. The laser dental device of claim 5, wherein said nonaqueous solution has a low vaporization point.

7. The laser dental device of claim 1, wherein said laser source includes at least one laser rod, said laser rod being positioned longitudinally within a center of said housing, said flashlamp being positioned parallel to said laser rod.

8. the laser dental device of claim 1, wherein said emission head includes a beam rotator at said first end of said emission head, said beam rotator comprising a central mirror and a rotating slidable adjustable outer mirror within a rotatable housing.

9. The laser dental device of claim 1, further comprising a mirror within said emission head for receiving and reflecting said laser beam, said mirror being pivotally mounted to allow for adjustment over a range of angles.

10. The laser dental device of claim 1, further comprising a mirror within said emission head for receiving and reflecting said laser beam wherein said mirror is concave.

11. A laser dental device comprising:
 a housing,
 a laser source including a flashlamp within said housing for generating a laser beam when said laser source is fired;
 an emission head having a first end and a second end wherein said first end is attached to said housing, said laser beam passing through said emission head to said second end; and
 a focus sensor attached to said second end of said emission head for positioning said emission head at a predetermined distance from a surface of a patient's mouth to be engaged by said laser beam, said focus sensor including a movable feeler member having an actuator that enables said laser source so that said laser source continuously fires when said emission head is within a range of distances that allow said laser source to engage the surface of a patient's mouth across the entire beam waist of said laser source; and
 a laser termination system comprised of at least one patient head rest pad, wherein each patient head rest pad has a sensor electrically coupled to said laser source for sensing a force applied to each patient head rest pad by the patient, said laser source being automatically terminated when an insufficient force is place upon said head rest pad by said patient.

12. A focus sensor for use on a laser dental device comprising:
 a housing having a first end and a second end, said housing having an opening at said first end defining an inner wall, said housing mountable to the laser dental device;
 a feeler mounted to said housing for reciprocating movement, said feeler having a first end and a second end, wherein said second end of said feeler extends through said opening at said first end of said housing;
 a pin attached to said second end of said feeler;
 a spring having a first end and a second end, wherein said first end of said spring is attached to said second end of said feeler, and said second end of said spring is attached to said inner wall of said housing;
 an actuator positioned within said housing and establishing contact that allows a laser source within the laser dental device to continuously fire at a range of distances from the surface to be engaged equal to the length of the beam waist of said laser source.

13. The focus sensor of claim 12, wherein said actuator provides continuous electrical contact over a range of positions of said feeler.

14. A laser dental device comprising:
 a housing;
 a laser source including a flashlamp within said housing for generating a laser beam when said laser source is fired;
 an emission head having a first end and a second end wherein said first end is attached to said housing, said laser beam passing through said emission head to said second end; and
 a focus sensor attached to said second end of said emission head for positioning said emission head at a predetermined distance from a surface of a patient's mouth to be engaged by said laser beam, said focus sensor including a movable feeler member having an actuator that enables said laser source so that said laser source continuously fires when said emission head is within a range of distances that allow said laser source to engage the surface of a patient's mouth across the entire beam waist of said laser source; and
 a locking system attached to said second end of said emission head for removably locking said emission head to the patient, said emission head including a beam rotator at said first end of said emission head, said beam rotator comprising a central mirror and a rotating slidable adjustable outer mirror within a rotatable housing, said laser locking system being electrically coupled to said laser source for automatically terminating said laser source when said locking system is disengaged;
 a cooling system electrically coupled with said laser source for cooling the surface of the patient's mouth by applying pulses of predetermined amounts of a nonaqueous solution to the surface of the patient's mouth; and
 a laser termination system comprised of at least one patient head rest pad, wherein each patient head rest pad has a sensor electrically coupled to said laser source for sensing a force applied to each patient head rest pad by the patient, said laser source being automatically terminated when insufficient force is placed upon said head rest pad.

15. A method of engaging a selected area of a mouth surface of a patient with laser radiation from a dental device, said dental device defining a laser radiation focal point, said method comprising the steps of:

positioning the dental device in proximate location with the mouth surface so that the laser radiation focal point is directed at the selected area of the mouth surface;

removably locking the dental device to the patient in said proximate location so that the laser radiation focal point remains directed at the selected area of the mouth surface;

engaging the selected area of the mouth surface with pulses of laser radiation;

sensing a patient's head within a head rest and sending a head rest signal to the dental device before engaging the selected area of the mouth surface with said pulses of laser radiation; and sensing the mouth surface and sending a distance signal to said dental device such that the pulses of laser radiation are only applied when a predetermined distance between the laser dental device and the mouth surface is sensed.

* * * * *